United States Patent [19]
Wilson

[11] Patent Number: 6,103,037
[45] Date of Patent: *Aug. 15, 2000

[54] METHOD FOR MAKING A CATHETER HAVING OVERLAPPING WELDS

[75] Inventor: James C. Wilson, Queensbury, N.Y.

[73] Assignee: Medi-Dyne Inc., Queensbury, N.Y.

[*] Notice: This patent is subject to a terminal disclaimer.

[21] Appl. No.: 08/951,627

[22] Filed: Oct. 16, 1997

Related U.S. Application Data

[63] Continuation of application No. 08/596,759, Feb. 5, 1996, abandoned, which is a continuation-in-part of application No. 08/570,941, Dec. 12, 1995, Pat. No. 5,772,641.

[51] Int. Cl.$^7$ .................................................. B65H 69/08
[52] U.S. Cl. .................. 156/158; 156/304.2; 156/304.6; 156/308.8; 264/248; 264/254; 264/255; 264/257
[58] Field of Search ................................ 264/230, 342 R, 264/257, DIG. 71, 248, 249, 254, 255, 259, 274; 156/157, 158, 304.2, 305.6, 308.2

[56] References Cited

U.S. PATENT DOCUMENTS

| | | |
|---|---|---|
| 3,924,632 | 12/1975 | Cook . |
| 3,945,867 | 3/1976 | Heller, Jr. et al. . |
| 3,962,153 | 6/1976 | Gore . |
| 3,965,909 | 6/1976 | Waddell et al. . |
| 4,044,765 | 8/1977 | Kline . |
| 4,052,989 | 10/1977 | Kline . |
| 4,305,983 | 12/1981 | Hoppe et al. . |
| 4,321,226 | 3/1982 | Markling . |
| 4,323,071 | 4/1982 | Simpson et al. . |
| 4,347,204 | 8/1982 | Takagi et al. . |
| 4,385,635 | 5/1983 | Ruiz . |
| 4,391,302 | 7/1983 | Huhn et al. . |
| 4,402,684 | 9/1983 | Jessup . |
| 4,425,919 | 1/1984 | Alston, Jr. et al. . |
| 4,430,083 | 2/1984 | Ganz et al. . |
| 4,430,282 | 2/1984 | Stack . |
| 4,430,283 | 2/1984 | Burnett et al. . |
| 4,447,239 | 5/1984 | Krütten . |
| 4,464,176 | 8/1984 | Wijayarathna . |
| 4,516,972 | 5/1985 | Samson . |
| 4,517,247 | 5/1985 | Suzuki et al. . |
| 4,531,943 | 7/1985 | Van Tassel et al. . |
| 4,547,193 | 10/1985 | Rydell . |

(List continued on next page.)

FOREIGN PATENT DOCUMENTS

| | | |
|---|---|---|
| 0 334 640 | 9/1989 | European Pat. Off. . |
| 2 043 201 | 10/1980 | United Kingdom . |
| 2 101 680 | 1/1983 | United Kingdom . |
| 2 156 680 | 10/1985 | United Kingdom . |
| WO 95/13110 | 5/1995 | WIPO . |
| WO 95/15780 | 6/1995 | WIPO . |

*Primary Examiner*—Jan H. Silbaugh
*Assistant Examiner*—Stefan Staicovici
*Attorney, Agent, or Firm*—Nixon & Vanderhye P.C.

[57] ABSTRACT

A method of forming a catheter comprising the steps of a) loading an inner layer on a mandrel; b) loading a reinforcing braid layer over the inner layer; c) adding a terminal tip to one end of the inner layer, the terminal tip applied directly over the inner layer with no portion of the reinforcing braid therebetween; d) loading a plurality of axial jacket sections over the braid layer, one of the axial jacket sections engaging an adjacent one of the plurality of axial jacket sections along a joint including substantially axially oriented seams; e) applying a shrink tube over the plurality of axial jacket sections and heating the shrink tube to cause the plurality of axial jacket sections to bond with each other, the braid layer and the inner layer; f) removing the shrink tube; and g) removing the mandrel. An aspect of the process relates to annealing an end of the braid layer and using a plastic sleeve compressed and melted about the annealed end to insure that the end of the braid layer lies flat on the inner layer. Where plural axial jacket sections are used, they are welded together by joints which include substantially axially oriented seams. In another embodiment, the axial jackets can be combined in a single coextruded, monolithic form having varying durometer and/or material compositions.

7 Claims, 5 Drawing Sheets

U.S. PATENT DOCUMENTS

| | | |
|---|---|---|
| 4,563,181 | 1/1986 | Wijayarathna et al. . |
| 4,577,543 | 3/1986 | Wilson . |
| 4,580,790 | 4/1986 | Doose . |
| 4,596,563 | 6/1986 | Pande . |
| 4,627,844 | 12/1986 | Schmitt . |
| 4,636,346 | 1/1987 | Gold et al. . |
| 4,648,892 | 3/1987 | Kittrell et al. . |
| 4,662,404 | 5/1987 | LeVeen et al. . |
| 4,665,604 | 5/1987 | Dubowik . |
| 4,690,175 | 9/1987 | Ouchi et al. . |
| 4,764,324 | 8/1988 | Burnham . |
| 4,790,831 | 12/1988 | Skribiski . |
| 4,793,351 | 12/1988 | Landman et al. . |
| 4,801,297 | 1/1989 | Mueller . |
| 4,813,930 | 3/1989 | Elliott . |
| 4,817,613 | 4/1989 | Jaraczewski et al. . |
| 4,836,872 | 6/1989 | Landry et al. . |
| 4,842,590 | 6/1989 | Tanabe et al. . |
| 4,846,814 | 7/1989 | Ruiz . |
| 4,861,337 | 8/1989 | George . |
| 4,863,442 | 9/1989 | DeMello et al. . |
| 4,886,506 | 12/1989 | Lovgren et al. . |
| 4,898,591 | 2/1990 | Jang et al. . |
| 4,898,702 | 2/1990 | Elkins et al. . |
| 4,899,787 | 2/1990 | Ouchi et al. . |
| 4,904,431 | 2/1990 | O'Maleki . |
| 4,925,710 | 5/1990 | Buck et al. . |
| 4,961,731 | 10/1990 | Bodicky et al. . |
| 5,005,587 | 4/1991 | Scott . |
| 5,017,259 | 5/1991 | Kohsai . |
| 5,037,404 | 8/1991 | Gold et al. . |
| 5,049,138 | 9/1991 | Chevalier et al. . |
| 5,057,092 | 10/1991 | Webster, Jr. . |
| 5,078,702 | 1/1992 | Pomeranz . |
| 5,105,819 | 4/1992 | Wollschläger et al. . |
| 5,147,315 | 9/1992 | Weber . |
| 5,156,155 | 10/1992 | King . |
| 5,160,559 | 11/1992 | Scovil et al. . |
| 5,171,232 | 12/1992 | Castillo et al. . |
| 5,207,960 | 5/1993 | Moret de Rocheprise . |
| 5,221,270 | 6/1993 | Parker . |
| 5,221,271 | 6/1993 | Nicholson et al. . |
| 5,234,416 | 8/1993 | Macaulay et al. . |
| 5,254,107 | 10/1993 | Soltesz . |
| 5,279,596 | 1/1994 | Castaneda et al. . |
| 5,308,342 | 5/1994 | Sepetka et al. . |
| 5,312,356 | 5/1994 | Engelson et al. . |
| 5,318,032 | 6/1994 | Lonsbury et al. . |
| 5,336,205 | 8/1994 | Zenzen et al. . |
| 5,348,536 | 9/1994 | Young et al. . |
| 5,358,493 | 10/1994 | Schweich, Jr. et al. . |
| 5,387,199 | 2/1995 | Siman et al. . |
| 5,401,257 | 3/1995 | Chevalier, Jr. et al. . |
| 5,403,292 | 4/1995 | Ju . |
| 5,441,489 | 8/1995 | Utsumi et al. . |
| 5,445,624 | 8/1995 | Jimenez . |
| 5,531,721 | 7/1996 | Pepin et al. . |
| 5,542,937 | 8/1996 | Chee et al. . |
| 5,545,149 | 8/1996 | Brin et al. ............................... 604/265 |
| 5,545,151 | 8/1996 | O'Connor et al. . |
| 5,571,073 | 11/1996 | Castillo . |
| 5,584,821 | 12/1996 | Hobbs et al. . |
| 5,603,705 | 2/1997 | Berg ....................................... 604/282 |

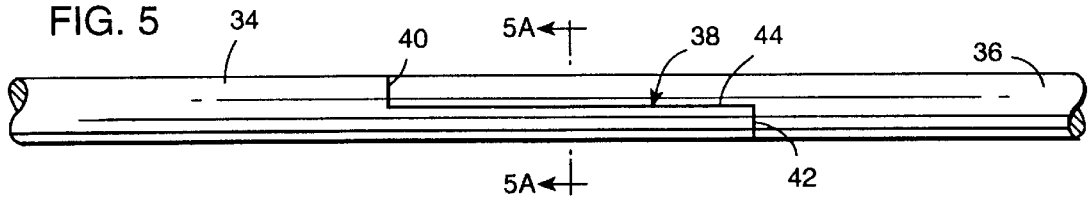
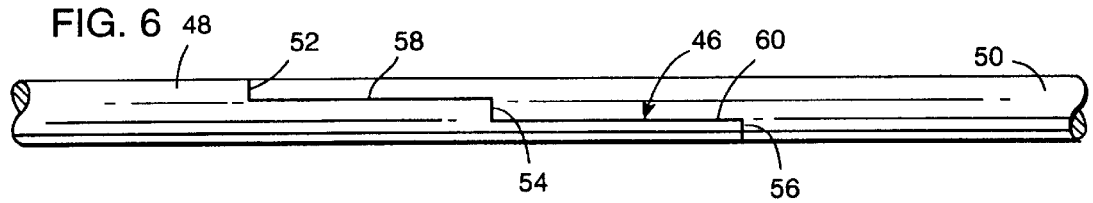
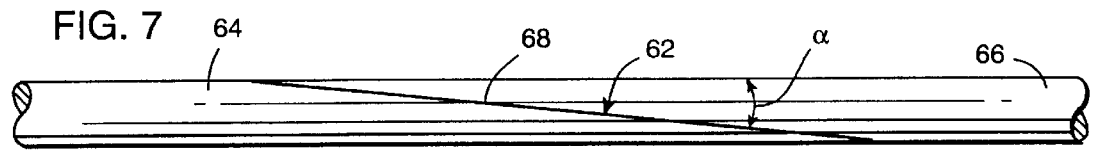
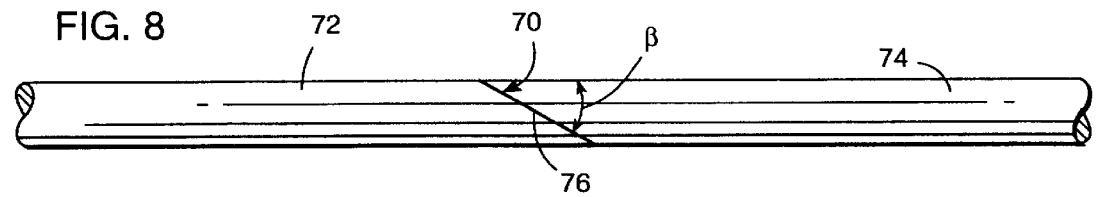
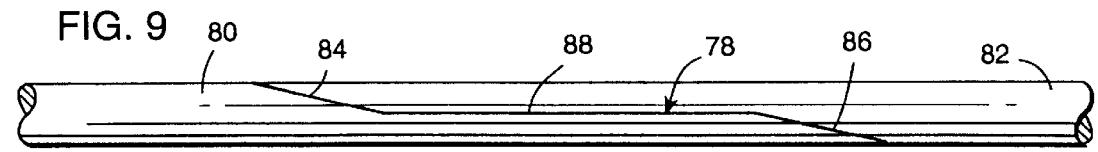
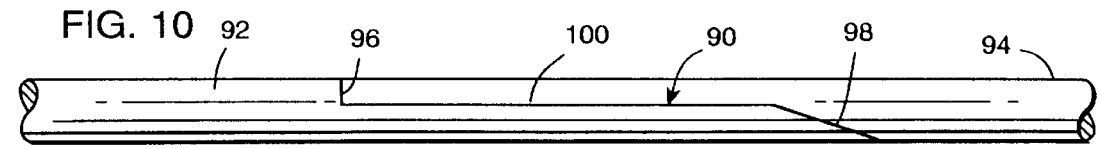

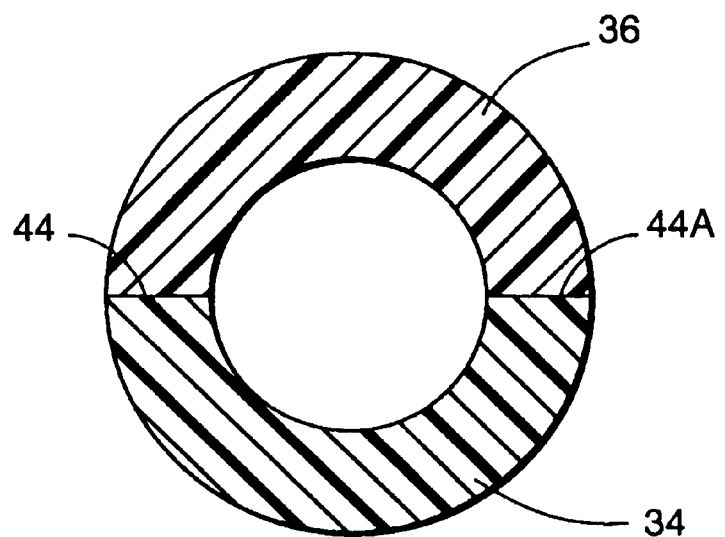
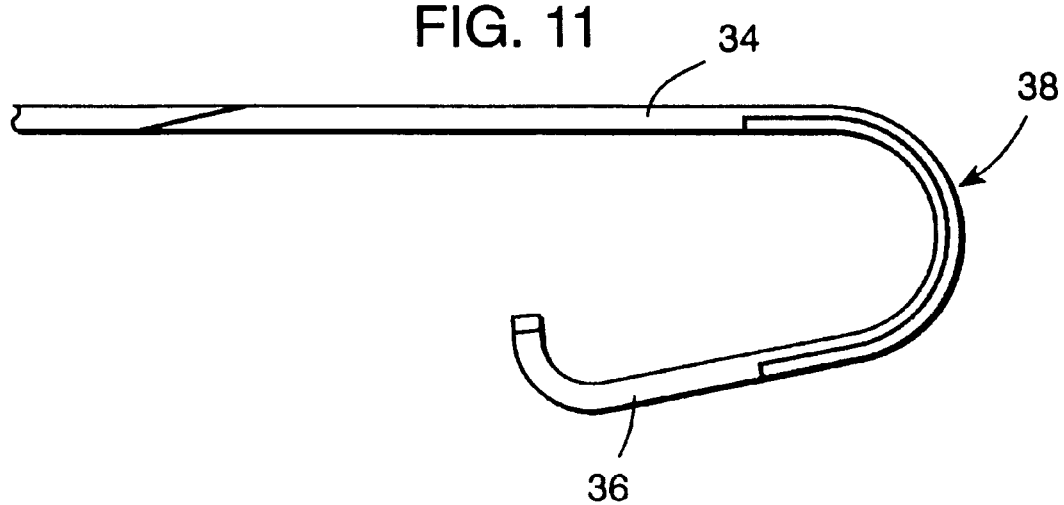

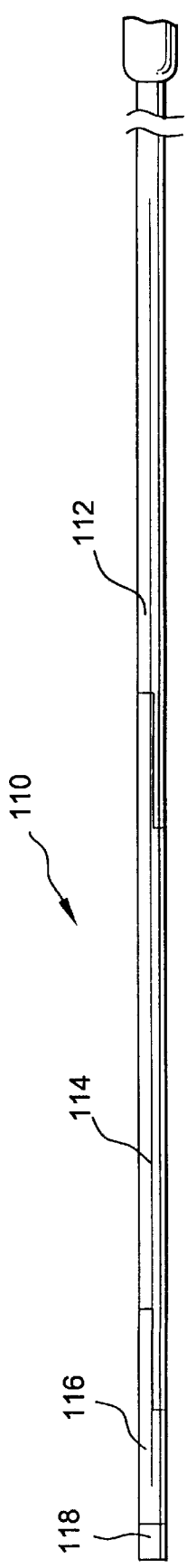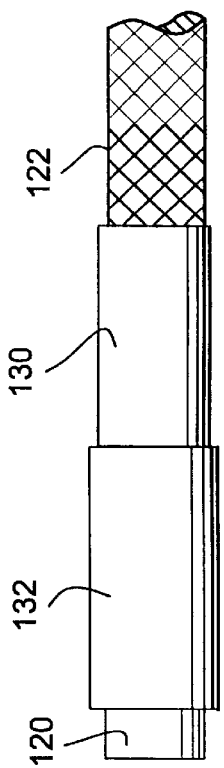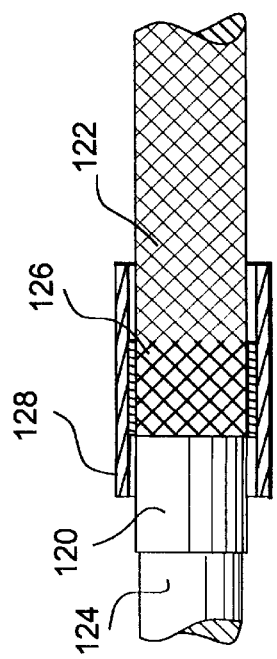
FIG. 12
FIG. 14
FIG. 13

METHOD FOR MAKING A CATHETER HAVING OVERLAPPING WELDS

RELATED APPLICATIONS

This is a continuation of application Ser. No. 08/596,759, filed Feb. 5, 1996, now abandoned, which is a continuation-in-part application of commonly owned application Ser. No. 08/570,941, entitled "Overlapping Welds For Catheter Constructions", filed Dec. 12, 1995, now U.S. Pat. No. 5,772,641, issued Jun. 30, 1998.

This invention relates generally to catheter constructions, and more particularly to welded joints between adjacent lengths of catheter material, as well as a related method of manufacturing such catheters.

BACKGROUND AND SUMMARY OF THE INVENTION

Currently, both diagnostic and therapeutic catheters are manufactured by forming braided tubes of stainless steel fibers or strands, over a mandrel. More specifically, the braided tube may be formed about an inner Teflon® liner or tube initially carried on a supporting mandrel. An outer plastic layer may then be extruded about the braided material to create the catheter body. Current catheter constructions also utilize a transition tip which is not reinforced with braid in order that the tip be softer and more flexible than the remaining portions of the catheter. In some catheter designs, an even more flexible tip (also referred to as the terminal tip) is bonded to the free end of the tubular transition tip.

Catheters which incorporate multiple axial sections typically employ butt or lap weld joints to secure the axial sections of the catheter together. See, for example, U.S. Pat. Nos. 5,254,107; 4,861,337; 4,793,351; 4,662,404; and 4,391,302. Some catheter constructions utilize a tapered joint where the terminal tip is joined to the catheter body. See, for example, U.S. Pat. Nos. 4,886,506 and 4,385,635.

Catheters incorporating either butt or lap type welded joints are not completely satisfactory however, and it is thus the object of this invention to improve upon prior catheter constructions by incorporating unique weld configurations which have a substantial axial seam component extending along the axis of the catheter. In other words, adjacent catheter sections (and not including the terminal tip) are cut and welded in such a way that they overlap in the longitudinal direction, but without altering the outer diameter of the catheter. This arrangement not only increases surface area at the weld joints and thereby also increases bond integrity, but also creates a more desirable transition between the same materials of different durometer or different materials with or without the same durometer, than other more conventional welds such as lap or butt welds.

The unique weld configurations of this invention also permit alteration of properties or characteristics of the catheter material in the area of the weld, and this feature is particularly advantageous in areas of the catheter that will be curved, in that different stiffness or hardness materials can be used on the inside and outside portions of the curve.

Examples of the unique weld configurations in accordance with this invention include step joints, taper joints, and combinations of the two.

This invention also relates to an improved method for manufacturing braid reinforced catheters with or without the unique axial weld joints as described above. In the exemplary embodiment, the process relates to the manufacture of a catheter having inner and outer layers sandwiched about a braided tube layer. The inner layer is preferably formed from Teflon® while the outer layer is provided in the form of three axial jacket sections, one of which comprises nylon and the others of which comprise a polyether block amid (PEBA), such as that commercially available under the name Pebax®.

In the process, a thin walled Teflon® tube is loaded onto a stainless steel mandrel. In a separate operation, a spring temper stainless steel wire is braided onto a disposable (preferably plastic) mandrel at a specified braid density and with a diameter approximating the diameter of the Teflon® covered mandrel described above. Predetermined lengths of the braided stock are cut and the disposable mandrel is removed and discarded. One end of the braided wire tube is then placed in an annealing fixture so that about a ½ inch long section of the braided tube is annealed. The annealed section is then trimmed to leave approximately a ¹⁄₁₆ inch long section of annealed braid.

Starting with the non-annealed end of the braided tube, the latter is loaded onto the Teflon® covered mandrel, sliding the annealed section over the end of the Teflon® tube so that approximately 1 inch of the Teflon® tube is left exposed. It is desirable to anchor the annealed section of the wire braid to the Teflon® tube, and this is done using a variety of methods including bonding the annealed wire section to the Teflon® using adhesives. In accordance with the present process, however, the annealed end portion of the wire braid is anchored to the Teflon® base using a sleeve of PEBA material applied with a shrink film such as FEP-Teflon. The compressive force generated by the shrink film, combined with the heat inherent in the process of shrinking the film, cause the PEBA sleeve to melt into the interstices of the wire braid at the same time that the wires are being forced flat against the inner Teflon® layer. This results in the annealed wires being held neatly in place so that they will not be disturbed during the remainder of the catheter assembly process. Using PEBA to achieve this end is desirable in that the various catheter components are kept as homogenous as possible.

In the next process step, a ½ inch length of soft terminal tip stock material is threaded over the end of the Teflon®/mandrel assembly so that it comes into contact with the end of the annealed portion of the wire braid described above. To keep the terminal tip in place, a tight press fitted piece of Teflon® tubing may be threaded onto the Teflon®/mandrel assembly and advanced until it is butted up against the tip stock. This so-called "bumper" will keep the tip stock in place during the remainder of the catheter process, and will also keep the terminal tip material from flowing out of the end of the assembly during the thermal processing which follows.

As mentioned above, the outer layer of the catheter consists of three different extruded sections of tubing which have specific wall thicknesses and inside diameters which are no smaller than the outside diameter of the wire braid. The primary jacket is formed from nylon 12 with 30% $BASO_4$, and it is approximately 80 cm. in length and forms the main shaft with the catheter. The secondary jacket is PEBA with a Shore D durometer of 70, and again with 30% $BASO_4$. This secondary jacket is approximately 25 cm. in length. A tertiary jacket is formed from a soft PEBA, with a Shore D durometer of 48 also with 30% $BASO_4$. This tertiary jacket is approximately 7 cm. in length and generally forms the soft primary curved section of the catheter. It should be noted, however, that PEBA could be substituted in part or all for the nylon 12, and the $BASO_4$ could consist of more or less than 30%, and other radio paque agents such as but not limited to bismuth subcarbonate and the like may be employed. The axial jackets are cut such that they can be joined using the axial seam weld constructions described above.

The tertiary jacket is first loaded onto the end of the braided tube and Teflon® inner layer assembly, opposite the end with the annealed section of wire braid and moved axially along the mandrel until it contacts the terminal tip stock. The secondary jacket is then loaded onto the assembly with its weld seam oriented as necessary to the corresponding weld seam of the tertiary jacket. The primary jacket is then loaded in the same fashion.

An FEP shrink tube is loaded over the entire catheter assembly, and the assembly is then placed into an oven or other heated chamber where the FEP shrink tube is heated, causing the now molten jackets to compress into the interstices of the wire braid, contacting and adhering to the etched surface of the Teflon® liner. After the assembly has cooled to room temperature, the FEP shrink tube and then the stainless steel mandrel are removed. Finally, the soft terminal tip stock can be cut to the desired length and any of a variety of known methods can be utilized to "reflow" the cut end of the tip such that the soft PEBA material flows beyond the end of the Teflon® liner, leaving the liner encapsulated by a small tip of PEBA material.

Other objects and advantages of the subject invention will become apparent from the detailed description which follows.

BRIEF DESCRIPTION OF THE DRAWINGS

FIG. 5 is a side elevation of a catheter incorporating a step weld in accordance with the present invention;

FIG. 5A is a section taken along the line 5A—5A of FIG. 5;

FIG. 6 is a side elevation of a catheter incorporating a multistep weld in accordance with the invention;

FIG. 7 is a side elevation of a catheter incorporating a shallow angle weld in accordance with the invention;

FIG. 8 is a side elevation of a catheter incorporating a steep angle weld in accordance with the invention;

FIG. 9 is a side elevation of a catheter incorporating a combination step/angle weld in accordance with the invention;

FIG. 10 is a side elevation of a catheter incorporating a combination step, angle and butt weld in accordance with the present invention;

FIG. 11 is a partial side elevation illustrating a catheter with multiple sections including a curved section incorporating a weld in accordance with the subject invention;

FIG. 12 is a partial side elevation of a catheter in accordance with the invention;

FIG. 13 is a partial side elevation illustrating the manner in which the end of a wire reinforcement braid is secured to an inner layer of a catheter during the manufacturing process;

FIG. 14 is a partial side elevation illustrating the manner in which a terminal tip is added to the forward end of the catheter during the manufacturing process;

DETAILED DESCRIPTION OF THE DRAWINGS

Figure 1:
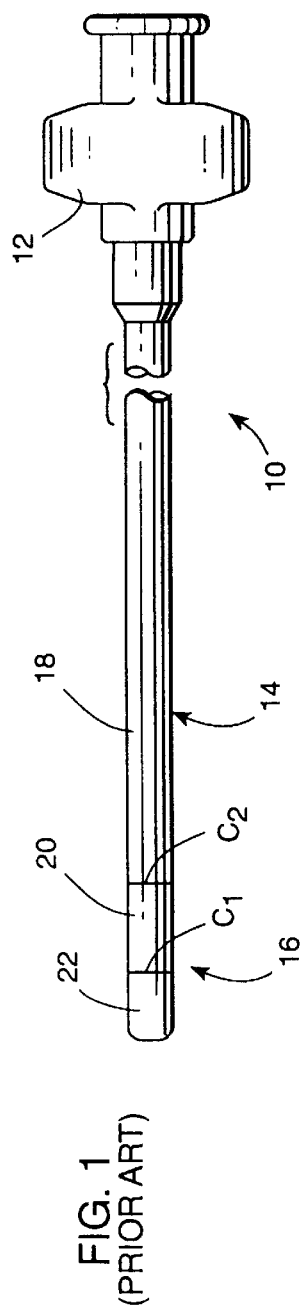
FIG. 1 is a side elevation, partly broken away, of a conventional catheter construction.
Figure 2:
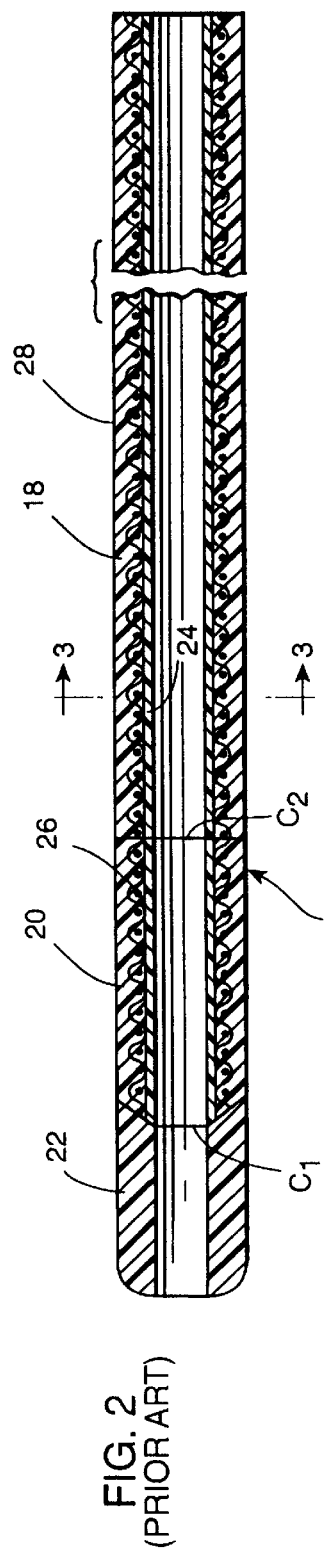
FIG. 2 is a side section of the distal end of the catheter shown in FIG. 1.

FIGS. 1 and 2 represent a known catheter construction of the type disclosed in U.S. Pat. No. 5,254,107. The catheter assembly 10 includes a conventional hub 12 at its proximal end, and a tubular catheter 14 extending from the hub 12 to a distal end 16. The catheter may have a first axial section 18, a second axial section 20 and a distal tip section 22.

The catheter 14 comprises an inner tubular plastic layer 24, which may be made of fluoro polymers such as PTFE, FEP or other similar polymers. A second layer 26 comprises a braided stainless steel tube applied by a conventional braiding machine. An outer, third layer 28 of plastic is then applied by suitable means over the braided layer. As disclosed in the '107 patent, this outer layer may include two or more axial sections. For example, the first axial section 18 may be made of a plastic material such as nylon 12 with a Shore D durometer of 65–70. The second axial section 20 may be nylon 12, and may have a Shore D durometer of 35–45. The transition tip 22 may be made of polyurethane with a Shore A durometer of about 80. In the '107 patent, the adjacent axial sections are butt welded or fused together, such that the joints describe circles C1 and C2 perpendicular to the longitudinal axis of the catheter. The inner plastic layer 24 extends through the first and second sections 18 and 20 but not through the third tip section 22.

The present invention relates to new and unique weld configurations for joining axial sections of the outer plastic layer of a catheter as generally described above.

Figure 4:
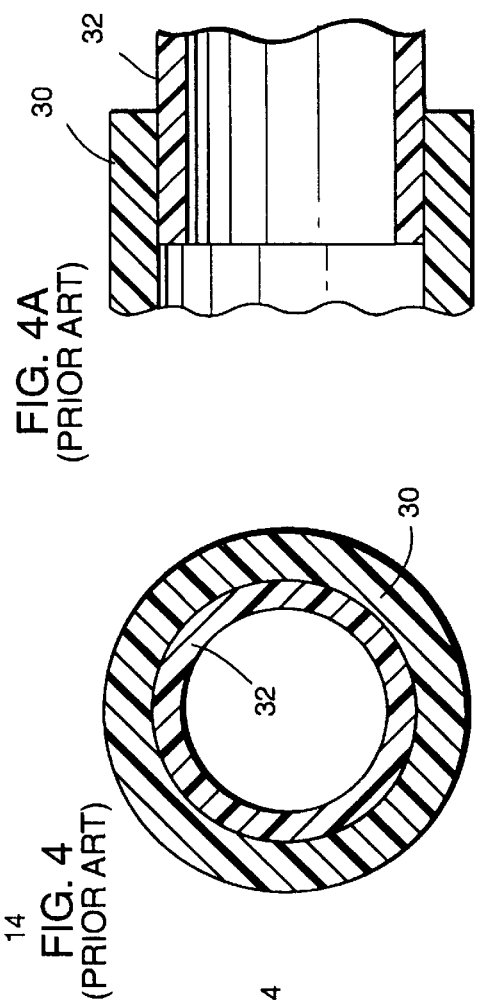
FIG. 4 is a cross section of a conventional lap weld in a catheter.
Figure 4A:
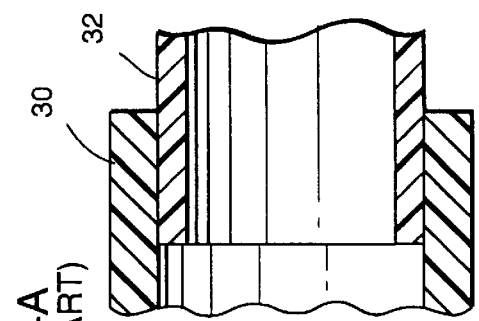
FIG. 4A is a partial side section of the welded joint illustrated in FIG. 4.

Conventional welds used in catheter constructions are either of the butt type shown in FIGS. 1 and 2, or of the overlapping variety, typically known as "lap" welds as shown in FIGS. 4 and 4A (inner layer and braided layer removed for the sake of clarity). Thus, one tubular portion 30 is received over a second tubular portion 32 and welded thereto, such that, in the weld area, a double thickness is created, as best seen in FIG. 4A.

In accordance with this invention, welds are used to connect lengths of catheter tubing, which welds are designed to have substantial axial length, but without altering the outer diameter of the catheter. In FIG. 5, for example, a first catheter length 34 is connected to a second catheter length 36 by a step weld 38 which includes radial seam portions 40 and 42 and extended axial seam portions 44, 44A (see FIG. 4A). Note there is no double thickness of material and no change in outside diameter. Here again, internal layers have been omitted simply for the sake of clarity.

In FIG. 6, a multi-step weld 46 axially joins catheter lengths 48 and 50, with the weld having three radial seam portions 52, 54 and 56 and two extended axial seam portions 58 and 60.

In FIG. 7, a shallow angle weld 62 axially joins catheter lengths 64 and 66. While no purely radial weld seam portions are formed in this arrangement, a single extended axial portion 68 gradually transitions along a shallow angle α.

FIG. 8 illustrates a variation in the weld configuration of FIG. 7, in that the weld 70 axially joining catheter lengths 72, 74 axially along a seam 76 which makes a relatively steep angle β.

FIG. 9 illustrates a hybrid weld 78 axially joining catheter lengths 80, 82 along a pair of angled seams 84, 86 connected by an extended axial seam 88.

FIG. 10 illustrates yet another hybrid weld 90 axially joining catheter lengths 92, 94. The weld includes a radial seam portion 96 and an angled seam portion 98 connected by an extended axial seam portion 100.

In each instance, the above described welds axially join two lengths of catheter with a significant axial seam portion (at least about 0.5 cm. in axial length and preferably 0.5–10 cm.) but without altering the outside diameter (OD) of the catheter. In other words, the OD of the outer plastic layer does not change and, in no case are there double thicknesses as in lap welds. At the same time, unlike butt welds, the weld seams extend axially along the length of the catheter. These extended axial portions of the various weld configurations (the longitudinal or axial extent of which may be varied) allow the catheter to be constructed with certain desired properties or characteristics as explained below.

The overall increased surface area of the welded joints increases the bond integrity between the two joined sections. The various weld configurations also create more desirable transitions between materials of different durometers, resins, etc. than typical butt or lap welded joints.

It is also possible to vary the characteristics of the catheter along its length by means of the overlapping welds described herein. For example, for the catheter shown in FIGS. 5 and 5A, with an axially. extended overlap of from, e.g., 0.5 to 10 cm., a unique section of catheter is created where section 34 might be a hard durometer (e.g., 60–70 on the Shore D Scale) and section 36 a soft durometer (e.g., 25–50 Shore D Scale or even a very soft Shore A hardness), the combined axial section along the axial length of the weld has a stiffness which is the average of the two durometers. This ability to create lengths of catheter with different properties or characteristics is most advantageous in areas of the catheter which will incorporate (or be bent into) curved areas.

With reference now to FIG. 11, which illustrates the catheter sections 34 and 36 in a curved state through the weld area 38, the length 34 has a harder durometer—on the outside of the curve; while the length 36 has a softer durometer—on the inside of the curve. As a result, not only does the weld overlap area have a desirable stiffness which falls between the stiffness of the materials used to form sections 34 and 36, but in addition, unique curve retention properties are created by reason of the dominance of the harder durometer over the softer durometer. This is merely one example of the many possible applications of the concept. It is quite possible, for example, that for a similar curved area with a different purpose, the softer durometer may be on the outside and the harder durometer on the inside of the curve. By altering the radial location of the axial seam of the weld, different percentages of harder and softer durometers can be employed. As a visual aid to distinguish catheter sections having different properties, the axially overlapping sections may be color coded.

It should also be pointed out that the different catheter lengths can be of the same material (e.g., suitable resins) but have different durometers, or they can be of different materials of the same or different durometer. Suitable resins include Nylon 11 and Nylon 12; Pebax® (25D to 70D); Nylon/Pebax® blends; polyurethanes (large durometer-infinite range); polyethylenes (high and low density); PVC; and other medical grade resins and various combinations of same.

Typical catheter constructions as shown and described herein may be in the size range of 1–15 French (0.013" to about 0.200" I.D.).

Figure 3:
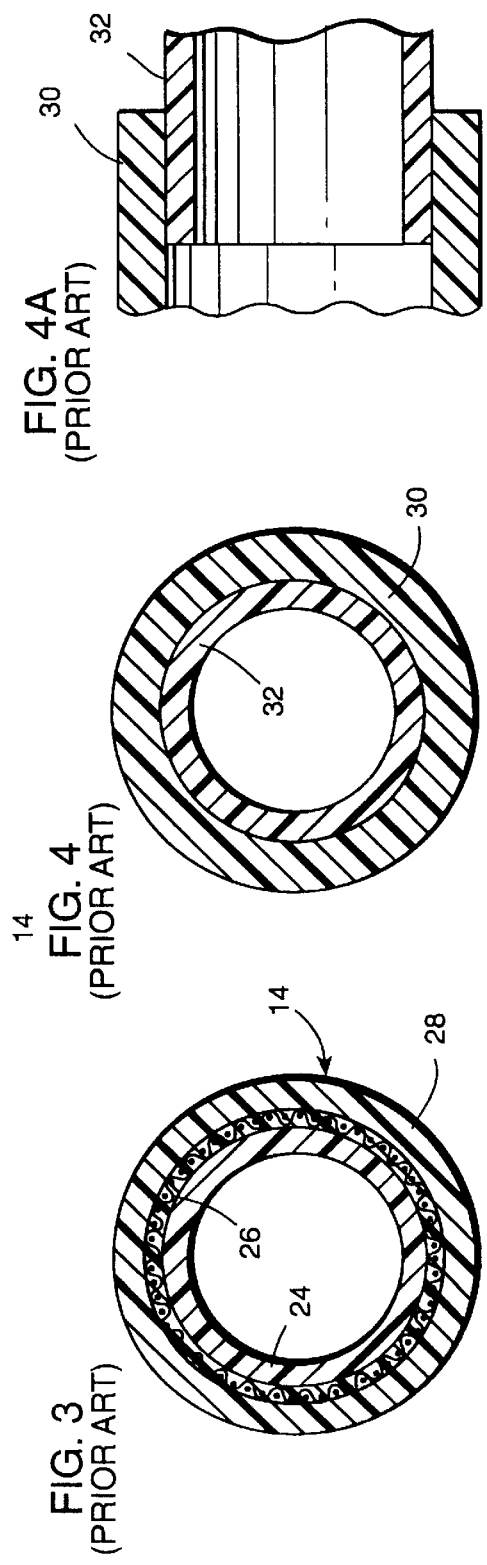
FIG. 3 is a section taken along the line 3—3 of FIG. 2.

One or more inner layers (omitted from FIG. 5A but similar to FIG. 3) may include, for example, a conventional PTFE (i.e. Teflon®), FEP or similar liner reinforced by stainless steel braid. The invention here is applicable, however, to a wide range of catheter types. For example, both diagnostic (angiography) and therapeutic (guiding) catheters (and other catheter technologies such as PTA, PTCA, electrophysiology, pacing leads, etc.) are suitable candidates for incorporation of the welds of this invention. Such catheters, as indicated above, may or may not include woven or braided reinforcements. Such reinforcements, if used, may comprise metal or synthetic materials including stainless steel, Kevlar®, etc. The catheters may be of single or multi-lumen design and may or may not have a Teflon® or other friction reducing lining. The catheters may or may not have a tapered distal portion and may or may not have side ports. While the catheter constructions illustrated herein show only a single weld per catheter, i.e., two axial sections, it should be understood that each catheter may have more than one welded area and may incorporate two or more different resins with the same or varying durometers.

With regard to the weld areas per se, the transition portions, i.e., he axially extending portions of the weld, may have an axial length to radial depth ratio of from about 3:1 to about 40:1. For purposes of discussion herein, a short transition weld has a ratio of about 3:1 to about 12:1, whereas a long transition weld has a ratio of about 12:1 to about 40:1. Short transition welds provide increased surface areas which strengthens the welded joints, and provide longer, less abrupt transition areas than simple butt welds. Such welds minimize the tendency of kinking and provide better torque transmission characteristics than conventional butt welds.

Long transition welds also provide increased surface area for strengthening the welded joints. In addition, long transition welds produce more desirable feel and/or handling characteristics in use. The orientation of different materials in long transition welds provides ease of straightening and permits unique properties to be established within one or more curved areas of the catheter. Long transition welds also allow for greater differences in durometer.

A preferred process for manufacturing catheters as generally described above will now be explained in detail. For purposes of explaining the process, a preferred catheter construction is shown at 110 in FIG. 12. The catheter includes three axial sections: a primary section 112, a secondary section 114, and a tertiary transition tip section 116. A terminal tip 118 is also secured at the distal end of the catheter. The catheter also includes an inner layer 120, preferably of Teflon®, and a stainless steel braid layer 122 sandwiched between the inner Teflon® layer 120 and the outer layer comprising jacket sections 112, 114 and 116 (see FIG. 13).

Initially, the thin walled, highly lubricious inner Teflon® layer 120 in thin tubular form, is loaded onto a generally rigid, preferably solid, ground stainless steel mandrel 124 of approximately 44" in length. The layer 120 may have a wall thickness of about 0.0015", and the exterior surface thereof is etched.

Separately, ultra spring temper stainless steel wire is braided onto a continuous length of a disposable (preferably plastic) mandrel (not shown). The braid density is approximately 60-PIC, and the mandrel has a diameter which approximates the diameter of the Teflon® covered mandrel described above. The braided stock is cut to a length of approximately 44", and the disposable mandrel then removed. One end of the cut braided tube or layer 122 is placed into an annealing fixture and, after annealing about a ½ inch section of the braided tube, the annealed section is cut so as to leave an annealed end of approximately ¹⁄₁₆" in length at one end of the braided tube 122.

Now, starting with its non-annealed end, the braided tube 122 is loaded onto the Teflon® covered mandrel, finally sliding the annealed end over the end of the mandrel 124 so that about 1 inch of Teflon® is left exposed (see FIG. 13). In other words, the ¹⁄₁₆" annealed end of the braided tube 122 lies adjacent a 1 inch exposed end of the Teflon® layer 120. It has been found that by annealing the end of the braided tube, the cut ends thereof will lie flat, in a relaxed state, on the Teflon layer 120. Otherwise, the cut ends would tend to spring outwardly and not only inhibit loading of the axial jacket sections, but also potentially damage the latter as well.

In order to facilitate loading of the axial jacket sections over the intermediate braided tube layer 122, it has also been found desirable to anchor the end of the wire braid layer or tube 122 to the Teflon® layer 120 to further facilitate loading the axial jacket sections. In a preferred arrangement in accordance with the process of this invention, the annealed end of the wire braid layer or tube 122 is anchored to the inner Teflon® layer 120 using a small, thin walled (0.002 inch) sleeve 126 of PEBA material. After the sleeve 126 is loaded onto the annealed end of the braided tube as shown in FIG. 13, a shrink film 128 is applied over the sleeve. The shrink film, which may be formed of FEP-Teflon®, is then heated so that the compressive force during shrinking, combined with the heat inherent in the process, causes the PEBA sleeve 126 to melt into the interstices of the braided layer 122, at the same time that the cut end wires are being forced flat against the Teflon® layer 120. This results in the end wires being held neatly in place so that they will not be disturbed during the remainder of the assembly process. The use of PEBA material for the sleeve 126 is particularly advantageous in that it retains the homogenous nature of the catheter components.

With reference now to FIG. 14, a length of soft tip material (which may be a softer PEBA material, e.g., a Shore D of about 30), in the form of a sleeve 130, is threaded over the end of the Teflon®) inner layer 120 so that it is in abutting contact with the annealed end of the braid layer as described above. In order to keep the tip sleeve 130 in place, a Teflon® tube 132 may be press fit over the Teflon® inner layer 120 and advanced until it butts up against the tip sleeve 130. This bumper will keep the tip in place during the remainder of the catheter processing, and will keep the tip material from flowing out of the forward end of the assembly during the remaining thermal processing described below.

The first or primary jacket section 112 (comprising the major length portion of the catheter) is formed in the exemplary embodiment from Nylon 12 with 30% BASO₄. This first axial section may have a length of approximately 80 cm. and forms the main shaft of the catheter. The secondary jacket 114 is formed from PEBA with a Shore D durometer of 70 and approximately 30% BASO₄. This secondary jacket has an axial length of about 25 cm. and forms what may be referred to as the Aortic curve section of the catheter. The tertiary jacket 116 is formed from a soft PEBA with a Shore D durometer of 48 and approximately 30% BASO₄. This tertiary jacket may have a length of about 7 cm. and forms the soft primary curve section of the catheter, also known as the transition tip.

The jacket sections 112, 114 and 116 are cut axially and loaded onto the braided assembly (inner layer 120 and braid layer 122) as follows.

Figure 15:
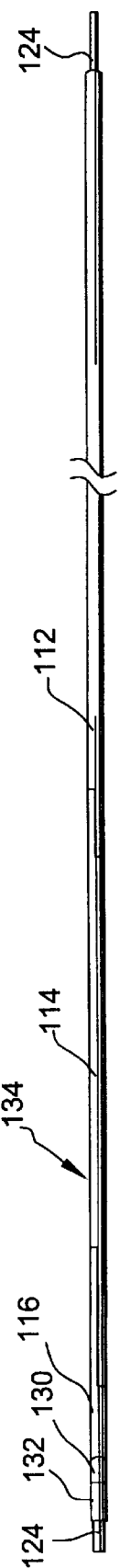
FIG. 15 is a side elevation of an assembled catheter in accordance with the process of this invention, prior to thermal processing.

First, the tertiary jacket 116 (the forwardmost jacket section of the catheter as seen in FIG. 15) is loaded onto the end of the braided assembly opposite the end with the annealed section of wire braid. This tertiary section 116 is moved along the braid layer 122 until it fully covers the annealed section of the braid, and contacts the tip stock sleeve 130 which ultimately forms the terminal tip 118. The secondary jacket 114 is then loaded onto the braided assembly such that the weld seams are aligned (as shown, for example, in FIGS. 5–10 depending on the specific weld or combinations of welds used). The primary jacket section 112 is then loaded onto the braid assembly in the same fashion.

Figure 16:
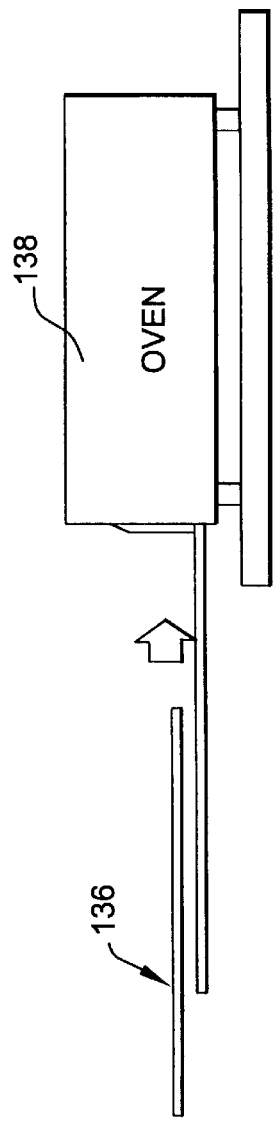
FIG. 16 is a schematic side elevation illustrating the catheter of FIG. 15, covered with a shrink tube, ready for thermal processing.

With the axial three jacket sections 112, 114 and 116 loaded onto the braided assembly, and with the weld type joints properly oriented, a length of FEP shrink tube 134 (see FIG. 15) of approximately 44 inches in length is placed over the entire catheter assembly, including the tip stock sleeve 130. The shrink tube used is usually a 1.4:1 to 1.6:1 shrink ratio, with dimensions that may differ depending on the size of the catheter being made. The catheter assembly 136 is then placed into an oven 138 (FIG. 16) or onto a conveyor which passes through a heated chamber. Using the appropriate time and temperature criteria, the FEP tube 134 is shrunk, causing the now molten primary, secondary and tertiary jackets 112, 114 and 116 to compress into the interstices of the braid layer 122, and thus also contact and adhere to the etched surface of the Teflon® layer 120 as well.

After the assembly has cooled to room temperature, the FEP shrink tube 134 is slit or perforated and peeled off the assembly, and the bumper 132 removed. The stainless steel mandrel 124 is then removed from the internal diameter of the assembly.

The terminal tip sleeve 130 is then cut to a desired length (approximately 2 mm) and then, using any of a variety of conventional methods, reflowed such that the soft PEBA material flows beyond the end of the Teflon® liner of layer 120. As a result, the end of the Teflon® layer 120 is encapsulated by the small terminal tip 118 of PEBA material (see FIG. 12), thus forming the terminal tip. This soft tip 118 will overlie the one inch exposed portion of the Teflon® layer 120 but it will not have any wire braid reinforcement.

The end result is a catheter shaft which has multiple durometer sections, continuous ultra spring stainless steel wire extending up to the soft tip, and a continuous Teflon® liner extending through the tip. The. catheter also contains the unique axially disposed welded sections as described earlier, imparting different properties to the catheter at the desired axial locations thereof, and particularly in the curved areas.

While the above process has been described in connection with a catheter having three discrete exterior axially oriented jacket sections, it is also possible to create a coextruded tube which contains different durometers and/or different material compositions in varying ratios at specific points along the tube, creating a gradual controllable change in section. For example, it is possible to have a coextruded tube which contains a generally stiff material such as, but not limited to, nylon 12 and a considerably softer material such as, but not limited to, a Pebax® 55D. The tube may have a wall thickness of 0.008 inches. The main length of the tube, which could represent the shaft of the catheter, would have a 0.008 inch wall which has a 7:1 ratio of nylon to Pebax® 55D, respectively. At the specific point along the length of the tube, this ratio would be varied at a desired rate until the desired ratio of nylon to Pebax® 55D is achieved, at, say, about 1:7. In this way, it is possible to form a monolithic tube with a constant wall thickness that has variable stiffness along its length. This monolithic tube could then become the jacket for the assembly in the process as otherwise described above.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of forming a catheter comprising the steps of:
   a) loading an inner layer on a mandrel;
   b) loading a reinforcing braid layer over the inner layer but leaving an axial end portion of the inner layer exposed;
   c) loading a terminal tip directly onto the exposed axial end portion of the inner layer, a rearward end of said terminal tip axially abutting said reinforcing braid layer such that said terminal tip lies on said inner layer with no portion of said reinforcing layer radially therebetween;
   d) loading a plurality of axial jacket sections over the reinforcing braid layer, one of said plurality of axial jacket sections engaging an adjacent one of said plurality of axial jacket sections along a joint including substantially axially oriented seams and a forwardmost of said jacket sections engaging said terminal tip;
   e) applying a shrink tube over said plurality of axial jacket sections and heating the shrink tube to cause adjacent axial jacket sections to bond to said braid layer and said inner layer;
   f) removing said shrink tube; and
   g) removing said mandrel.

2. The method of claim 1 wherein a first of said plurality of jacket sections is made of nylon and wherein at least a second of said plurality of axial jacket sections is made of a blend of nylon and a polyether block amid.

3. The method of claim 2 wherein said second of said axial jacket sections has a Shore D durometer of about 48.

4. The method of claim 3 including a third axial jacket section, also formed of a blend of nylon and a polyether having a Shore D durometer of about 40.

5. The method of claim 4 wherein said first of said plurality of axial jacket sections has a Shore D durometer of about 70.

6. The method of claim 1 wherein said terminal tip is formed of a polyether block amid with a Shore D durometer of about 30.

7. The method of claim 1 wherein said terminal tip is joined to said forwardmost of said axial jacket sections using a butt joint.

* * * * *